(12) United States Patent
Todo et al.

(10) Patent No.: US 11,209,387 B2
(45) Date of Patent: Dec. 28, 2021

(54) GAS SENSOR ELEMENT AND GAS SENSOR

(71) Applicant: DENSO CORPORATION, Kariya (JP)

(72) Inventors: Yusuke Todo, Kariya (JP); Mitsunobu Nakato, Kariya (JP); Hiroki Ichikawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 270 days.

(21) Appl. No.: 16/062,879

(22) PCT Filed: Dec. 9, 2016

(86) PCT No.: PCT/JP2016/086703
§ 371 (c)(1),
(2) Date: Jun. 15, 2018

(87) PCT Pub. No.: WO2017/104564
PCT Pub. Date: Jun. 22, 2017

(65) Prior Publication Data
US 2019/0004008 A1   Jan. 3, 2019

(30) Foreign Application Priority Data

Dec. 17, 2015 (JP) .............................. JP2015-246438
Nov. 16, 2016 (JP) .............................. JP2016-223352

(51) Int. Cl.
*G01N 27/419* (2006.01)
*G01N 27/407* (2006.01)
*G01N 33/00* (2006.01)
*G01N 27/404* (2006.01)
(Continued)

(52) U.S. Cl.
CPC ......... *G01N 27/419* (2013.01); *G01N 27/406* (2013.01); *G01N 27/4045* (2013.01);
(Continued)

(58) Field of Classification Search
CPC ............. G01N 27/419; G01N 27/4075; G01N 27/406; G01N 27/416; G01N 27/4045;
(Continued)

(56) References Cited

U.S. PATENT DOCUMENTS 4,940,528 A * 7/1990 Oki ...................... G01N 27/407
204/426
5,877,406 A    3/1999 Kato
(Continued)

FOREIGN PATENT DOCUMENTS

EP    1731903 A1 * 12/2006 ......... G01N 27/4075
EP    1731903 A1 † 12/2006
(Continued)

OTHER PUBLICATIONS

Japan Patent Office, Office Action in corresponding JP Application No. 2016-223352, dated Dec. 20, 2018, published Jan. 8, 2019 (see Global Dossier).†

*Primary Examiner* — J. Christopher Ball
(74) *Attorney, Agent, or Firm* — Nixon & Vanderhye P.C.

(57) ABSTRACT

A gas sensor element including a solid electrolyte body, a sensor electrode, and a reference electrode is provided. The solid electrolyte body has oxygen ion conductivity and includes a measurement gas surface to be exposed to a measurement gas introduced from the exterior and a reference gas surface to be exposed to a reference gas introduced from the exterior. The sensor electrode is provided on the measurement gas surface of the solid electrolyte body. The reference electrode is provided on the reference gas surface of the solid electrolyte body. The sensor electrode includes a porous body containing a solid electrolyte having oxygen ion conductivity and a precious metal, the peak pore size of the sensor electrode being 0.03 μm to 0.3 μm.

5 Claims, 10 Drawing Sheets

(51) Int. Cl.
*G01N 27/416* (2006.01)
*G01N 27/406* (2006.01)

(52) U.S. Cl.
CPC ..... *G01N 27/4071* (2013.01); *G01N 27/4074* (2013.01); *G01N 27/4075* (2013.01); *G01N 27/4077* (2013.01); *G01N 27/416* (2013.01); *G01N 33/0037* (2013.01)

(58) Field of Classification Search
CPC ........... G01N 33/0037; G01N 27/4071; G01N 27/4074; G01N 27/4077
See application file for complete search history.

(56) References Cited

U.S. PATENT DOCUMENTS

| | | | |
|---|---|---|---|
| 5,948,964 | A | 9/1999 | Kato |
| 6,365,036 | B1 * | 4/2002 | Polikarpus ......... G01N 27/4075 204/424 |
| 2004/0000479 | A1 † | 1/2004 | Katafuchi |
| 2006/0231397 | A1 | 10/2006 | Nakagaki et al. |
| 2009/0242401 | A1 | 10/2009 | Horisaka et al. |
| 2014/0311906 | A1 † | 10/2014 | Oya |

FOREIGN PATENT DOCUMENTS

| | | | |
|---|---|---|---|
| JP | 2001-99810 | | 4/2001 |
| JP | 2012-52901 | | 3/2012 |
| JP | 2012052901 A | † | 3/2012 |
| JP | 2013-104737 | | 5/2013 |
| JP | 2014-145607 | | 8/2014 |

\* cited by examiner
† cited by third party

GAS SENSOR ELEMENT AND GAS SENSOR

This application is the U.S. national phase of International Application No. PCT/JP2016/086703 filed Dec. 9, 2016, which designated the U.S. and claims priority to JP Patent Application No. 2015-246438 filed Dec. 17, 2015, and JP Patent Application No. 2016-223352 filed Nov. 16, 2016, the entire contents of each of which are hereby incorporated by reference.

TECHNICAL FIELD

The present disclosure relates to a gas sensor element having a sensor electrode including a porous body, and to a gas sensor including the gas sensor element.

BACKGROUND ART

A gas sensor including a gas sensor element is used to detect the concentration of a specific gas contained in a measurement gas. The gas sensor element includes a solid electrolyte body having oxygen ion conductivity and a pair of electrodes formed on the solid electrolyte body. The gas sensor element is used for a NOx sensor, an A/F sensor, or an oxygen sensor, depending on the type of a detection gas. The solid electrolyte body has formed thereon at least a sensor electrode exposed to the measurement gas and a reference electrode exposed to a reference gas.

The sensor electrode is required be highly reactive with a specific gas to be detected. For example, a Pt—Rh alloy, which is highly reactive with a nitrogen oxide (NOx), is used for a sensor electrode of an element for a NOx sensor. However, a gas sensor element has a relatively large range of operating temperature (e.g. −40° C. to 850° C.), and thus expansion and contraction are likely to occur repeatedly in an electrode containing metal. Consequently, internal forces are likely to be generated in the electrode, which may cause peeling.

Patent Literature 1, for example, discloses a porous electrode whose peak pore size is adjusted to 0.31 μm or more and less than 1.1 μm. This predetermined peak pore size allows the porous electrode to sufficiently relax internal forces in the electrode through pores. Thus, peeling of the electrode is prevented.

CITATION LIST

Patent Literature

[PTL 1] JP 4416551 B

SUMMARY OF THE INVENTION

Technical Problem

However, a porous electrode with a relatively large peak porosity, as described above, is likely to have low reactivity with a detection gas. That is, an increase in the peak pore size of the electrode is advantageous for relaxing of internal forces. However, a three-phase interface between metal, solid electrolyte, and gas decreases, leading to fewer reactive sites of the detection gas. This results in, for example, a lower efficiency in converting detection gas molecules, such as NOx or $O_2$, into ions, such as oxygen ions. The lower efficiency increases an electrode interface resistance, which may increase a detection error. Consequently, variations in the sensor output of a gas sensor may increase.

The present disclosure has been made in view of the problem, and provides a gas sensor element and a gas sensor capable of sufficiently stabilizing a sensor output.

Solution to Problem

One aspect of the present disclosure is a gas sensor element (1), comprising at least:
a solid electrolyte body (2) having oxygen ion conductivity and including a measurement gas surface (21) to be exposed to a measurement gas ($G_1$) introduced from the exterior and a reference gas surface (22) to be exposed to a reference gas ($G_0$) introduced from the exterior; a sensor electrode (3) provided on the measurement gas surface of the solid electrolyte body; and a reference electrode (41) provided on the reference gas surface of the solid electrolyte body, wherein
the sensor electrode includes a porous body containing a solid electrolyte (31) having oxygen ion conductivity and a precious metal (32), the peak pore size of the sensor electrode being 0.03 μm to 0.3 μm.

Another aspect of the present disclosure is a gas sensor (6) including the gas sensor element.

Advantageous Effects of the Invention

In the gas sensor element and the gas sensor, the peak pore size of a sensor electrode including a porous body is adjusted within the specific small range. This increases the three-phase interface between a measurement gas, a precious metal in the sensor electrode, and a solid electrolyte. Thus, the measurement gas can be converted to ions in the sensor electrode with greater efficiency. This reduces the electrode interface resistance of the sensor electrode, leading to fewer detection errors of the gas sensor element. Consequently, variations in the sensor output of the gas sensor are minimized, which sufficiently stabilizes the sensor output.

As described above, the aspect provides a gas sensor element and a gas sensor capable of stabilizing a sensor output. Note that the reference signs in parentheses in the Claims and the Solution to Problem indicate correspondence with the specific means described in the following embodiments, and do not limit the technical scope of the present disclosure.

DESCRIPTION OF THE EMBODIMENTS

First Embodiment

Figure 3:
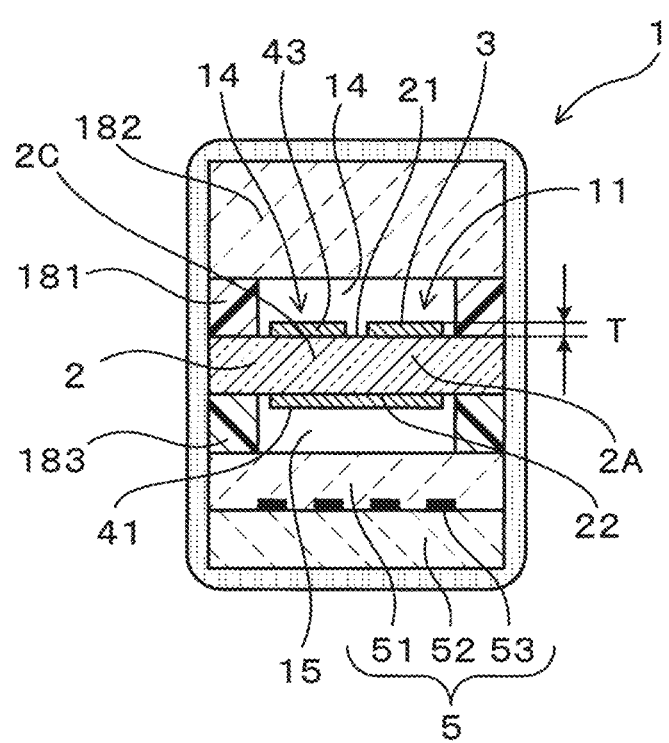
FIG. 3 is a cross-sectional view taken along III-III of FIG. 1.
Figure 4:
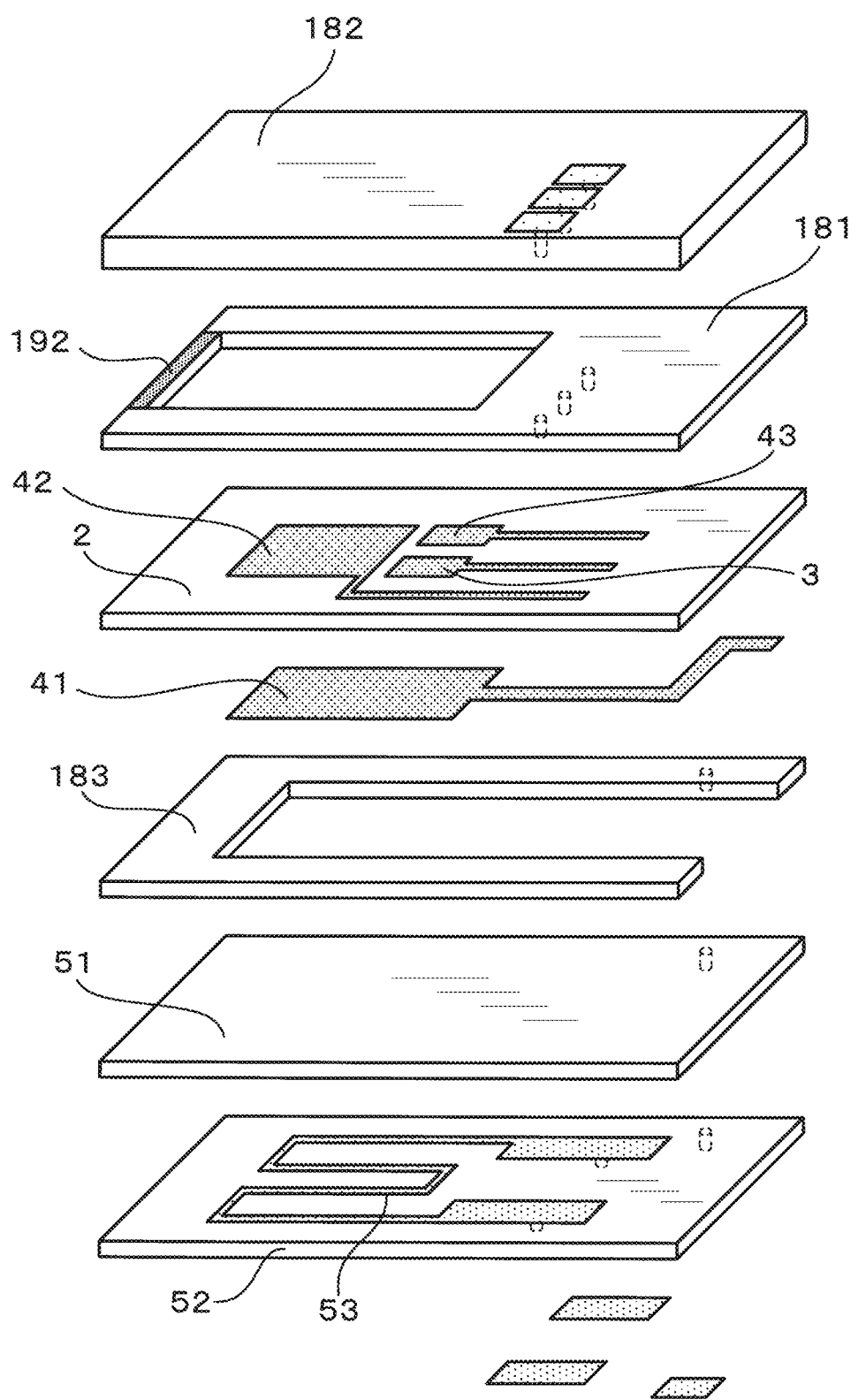
FIG. 4 is an exploded perspective view of the gas sensor element, according to the first embodiment.
Figure 5:
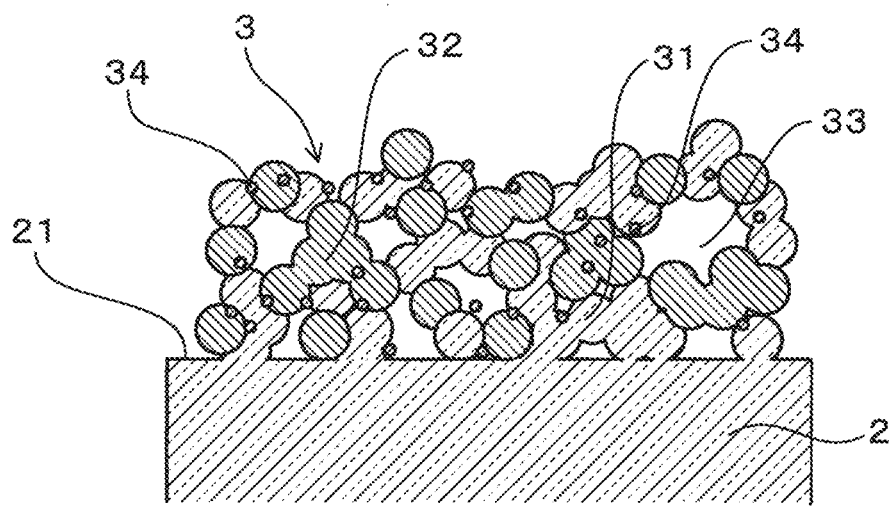
FIG. 5 is a cross-sectional view of a sensor electrode formed on a solid electrolyte body, according to the first embodiment.

An embodiment of a gas sensor element will be described with reference to FIGS. 1 to 7. As shown in FIGS. 1 to 4, a gas sensor element 1 of the present embodiment includes at least a solid electrolyte body 2 having oxygen ion conductivity, a sensor electrode 3, and a reference electrode 41. The solid electrolyte body 2 is a plate-like body including a measurement gas surface 21 and a reference gas surface 22. The measurement gas surface 21 is a surface to be exposed to a measurement gas $G_1$ introduced from the exterior of the gas sensor element 1. The reference gas surface 22 is a surface to be exposed to a reference gas $G_0$ introduced from the exterior. The sensor electrode 3 is formed on the measurement gas surface 21 of the solid electrolyte body 2, and the reference electrode 41 is formed on the reference gas surface 22. As shown in FIG. 5 and FIG. 7, the sensor electrode 3 includes a porous body containing a solid electrolyte 31 having oxygen ion conductivity, a precious metal 32, and a large number of pores 33. Furthermore, the peak pore size of the sensor electrode 3 ranges from 0.03 to 0.3 μm. The configuration of the gas sensor element 1 will be described in more detail below.

Figure 1:
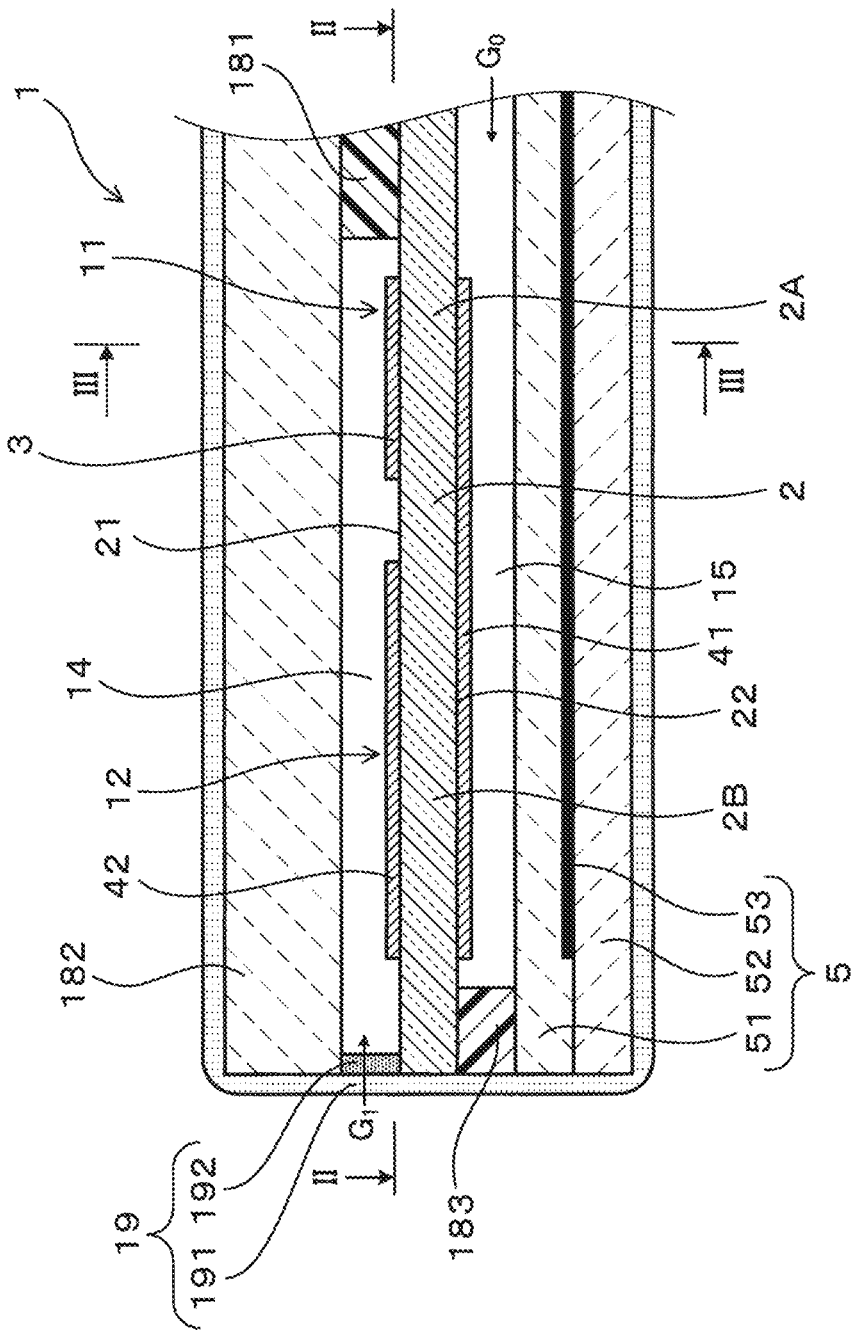
FIG. 1 is a cross-sectional view of a gas sensor element, according to a first embodiment.
Figure 2:
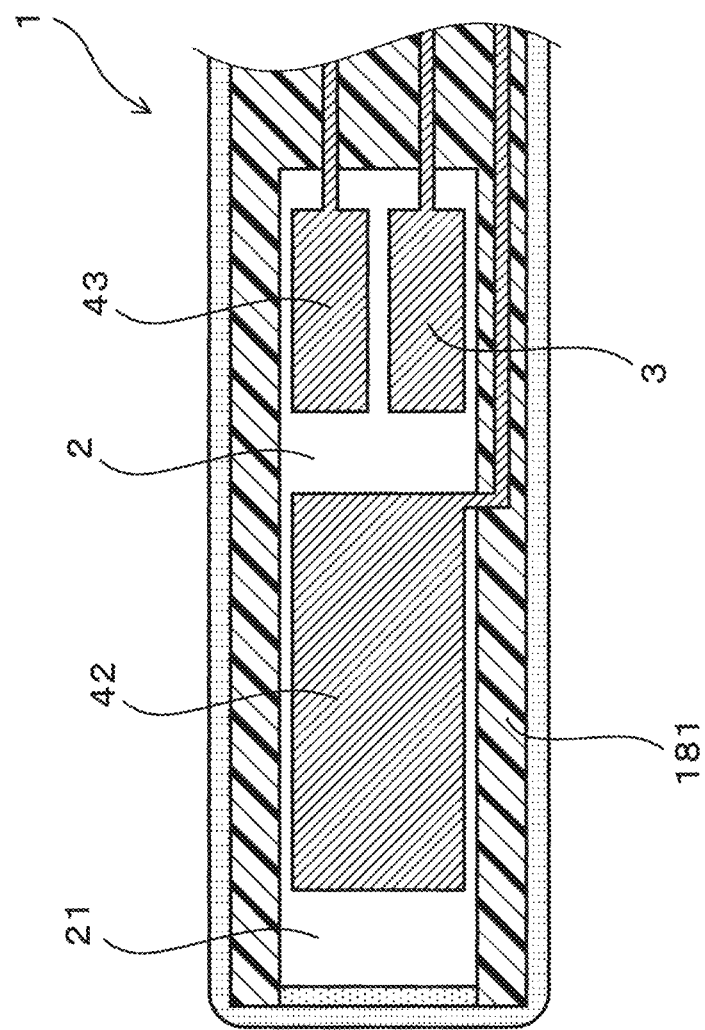
FIG. 2 is a cross-sectional view taken along II-II line of FIG. 1.

As shown in FIGS. 1 to 4, the gas sensor element 1 of the present embodiment is used for a NOx sensor that detects the concentration of NOx contained in an exhaust gas which is the measurement gas $G_1$. The solid electrolyte body 2 includes ceramics having oxygen ion conductivity. Examples of such ceramics include zirconia, yttria, and yttria-stabilized zirconia (YSZ); preferably, YSZ is used. The solid electrolyte body 2 is a plate-like body, and the measurement gas surface 21 and the reference gas surface 22 of the solid electrolyte body 2 are positioned to face each other. As shown in FIG. 2, the sensor electrode 3, a pump electrode 42, and a monitor electrode 43 are formed on the measurement gas surface 21. The electrodes 3, 42 and 43 are formed in different regions of the measurement gas surface 21.

The reference electrode 41 is formed on the reference gas surface 22 of the solid electrolyte body 2. As shown in FIGS. 1 and 3, a region 2A of the solid electrolyte body 2 is sandwiched between the sensor electrode 3 and the reference electrode 41, to form a sensor cell 11 including the sensor electrode 3, the region 2A of the solid electrolyte body, and the reference electrode 41. As shown in FIG. 1, a region 2B of the solid electrolyte body 2 is sandwiched between the pump electrode 42 and the reference electrode 41, to form a pump cell 12 including the pump electrode 42, the region 2B of the solid electrolyte body 2, and the reference electrode 41. As shown in FIG. 3, a region 2C of the solid electrolyte body 2 is sandwiched between the monitor electrode 43 and the reference electrode 41. The monitor cell 13 is formed of the monitor electrode 43, the region 2C of the solid electrolyte body, and the reference electrode 41.

As shown in FIG. 5, the sensor electrode 3 includes a porous body containing the solid electrolyte 31 having oxygen ion conductivity and the precious metal 32. Examples of the solid electrolyte 31 include zirconia, yttria, and YSZ; preferably, YSZ is used. The precious metal 32 preferably contains Pt as a main component, and may further contain at least one selected from the group consisting of Rh, Pd, Fe, Co, and Ni. In that case, the sensor electrode 3 has higher sensitivity with respect to NOx, making the gas sensor element suitable for a NOx sensor. To further increase the sensitivity of the sensor electrode 3 with respect to NOx, the precious metal 32 is preferably an alloy containing at least Pt and Rh.

As shown in FIG. 5, the sensor electrode 3 has a large number of pores 33. The porosity of the sensor electrode 3 can be adjusted, for example, within a range of 5 to 15%. This adjustment ensures sufficient electrical conductivity while preventing the sensor electrode from peeling. The porosity is defined as a ratio of the volume of pores in an actual electrode to the total volume of a region occupied if the electrode is assumed to be fully dense. The porosity can be measured by performing image processing on a scanning electron microscope (SEM) image of a cross-section of the sensor electrode 3.

The peak pore size of the sensor electrode 3 ranges from 0.03 to 0.3 μm. Adjustment of the peak pore size within this range increases the reactivity of the sensor electrode 3 while preventing conduction failure. The peak pore size will be described in detail in Example 1.

The reference electrode 41, pump electrode 42, and monitor electrode 43 are each formed of, for example, precious metal, and preferably contain at least Pt. Preferably, the pump electrode 42 and the monitor electrode 43 contain Pt and Au. In this case, adjusting the content of Au can increase reactivity to $O_2$ while reducing reactivity to NOx. Specifically, increasing the content of Au reduces reactivity to NOx, while reducing the content of Au increases reactivity to $O_2$. The reference electrode 41 preferably contains Pt as a precious metal. Furthermore, the electrodes 41, 42, and 43 may further contain a solid electrolyte as with the sensor electrode 3. Each of the electrodes 41, 42, and 43 may be a dense body having substantially no pores or a porous body such as the sensor electrode 3. If the electrodes 41, 42, and 43 are porous bodies, the porosity and the peak pore size can be adjusted within the same range as that of the sensor electrode 3.

As shown in FIGS. 1 and 3, an insulator 182 is laminated over the measurement gas surface 21 of the solid electrolyte body 2 with a first spacer 181 therebetween. The measurement gas surface 21 defines a measurement gas chamber 14 surrounded by the solid electrolyte body 2, first spacer 181, and insulating body 182. The measurement gas chamber 14 faces the pump electrode 42, sensor electrode 3, and monitor electrode 43. The measurement gas $G_1$ is introduced into the measurement gas chamber 14 from the exterior.

A heater 5 is laminated over the reference gas surface 22 of the solid electrolyte body 2 with a second spacer 183 therebetween. The reference gas surface 22 defines a reference gas chamber 15 surrounded by the solid electrolyte body 2, second spacer 183, and heater 5. The reference gas chamber 15 faces the reference electrode 41, and the reference gas $G_0$ is introduced into the reference gas chamber 15 from the exterior. The reference gas $G_0$ is, for example, air. The heater 5 is formed of two ceramic substrates 51 and 52 and a conductive layer 53 formed between the substrates 51 and 52. The conductive layer 53 generates heat by energization. Each of the first spacer 181, insulating body 182, second spacer 183, and ceramic substrates 51 and 52 includes ceramics, such as alumina.

As shown in FIG. 1, the gas sensor element 1 has a gas introduction part 19 for introducing the measurement gas $G_1$ into the measurement gas chamber 14. The gas introduction part 19 is provided at one end of the long gas sensor element 1 in a longitudinal direction. The gas introduction part 19 includes a trap layer 191 and a diffusion layer 192. The trap layer 191 traps toxic substances contained in the measurement gas $G_1$. The diffusion layer 192 limits the inlet velocity of the measurement gas $G_1$. Each of the trap layer 191 and the diffusion layer 192 is a porous body including ceramics, such as alumina. The trap layer 191 covers the entire surface of the gas sensor element 1. The diffusion layer 192 is formed at an open end of the measurement gas chamber 14.

The measurement gas $G_1$ is introduced from the gas introduction part 19 into the measurement gas chamber 14. The measurement gas $G_1$ is referred to as gas $G_1$ below. The gas $G_1$ is, for example, an exhaust gas. When the gas $G_1$ passes through the gas introduction part 19, toxic substances are trapped in the trap layer 191, and the inlet velocity of the gas $G_1$ into the measurement gas chamber 14 is controlled in the diffusion layer 192.

The gas $G_1$ introduced into the measurement gas chamber 14 passes over the pump electrode 42 and arrives at the sensor electrode 3 and the monitor electrode 43. When the gas $G_1$ passes over the pump electrode 42, oxygen in the gas $G_1$ is decomposed to generate oxygen ions in the pump cell 12. The pump cell 12 is constituted by the electrode 42, electrode 41, and region 2B of the solid electrolyte body 2. The oxygen ion is discharged through the solid electrolyte body 2 into the reference gas chamber 15. Thus, the concentration of oxygen in the gas $G_1$ introduced from the gas introduction part 19 is adjusted in the pump cell 12, and the oxygen concentration decreases as the gas $G_1$ approaches the sensor electrode 3.

In the sensor electrode 3, NOx in the gas $G_1$ is decomposed to generate oxygen ions. The concentration of NOx in the gas $G_1$ can be detected by measuring a sensor current Is in the sensor cell 11. The sensor cell 11 is constituted by the sensor electrode 3, reference electrode 41, and region 2A of the solid electrolyte body 2. The sensor current Is is generated when the oxygen ion flows through the solid electrolyte body 2. In the gas $G_1$ arriving at the sensor electrode 3, a slight amount of oxygen not removed by the pump cell 12 may remain. The oxygen concentration is measured by the monitor cell 13, and this measured value is used for correction of the NOx concentration measured in the sensor cell 11. The monitor cell 13 is constituted by the monitor electrode 43, reference electrode 41, and region 2C of the solid electrolyte body 2. That is, oxygen is decomposed by the monitor electrode 43, and a monitor current Im generated when the oxygen flows through the solid electrolyte body 2 is measured in the monitor cell 13. Then, the monitor current Im is subtracted from the sensor current Is. This configuration allows NOx concentration to be accurately measured without being affected by the residual $O_2$.

The gas sensor element 1 is manufactured in the following manner. Specifically, as shown in FIG. 4, electrode materials A are printed on a ceramic sheet that constitutes the solid electrolyte body 2 after baking. The electrode materials A are used to form the electrodes 3, 41, 42, and 43. In the following description, an upper part and a lower part of FIG. 4 are referred to as an upper side and a lower side, respectively. On the upper side of the ceramic sheet for the solid electrolyte body 2, ceramic sheets are sequentially laminated that constitute the first spacer 181, the diffusion layer 192, and the insulating body 182 after baking. On the lower side of the ceramic sheet for the solid electrolyte body 2, a ceramic sheet that constitutes the second spacer 183 is laminated. On the lower side of the ceramic sheet for the second spacer 183, a ceramic sheet that constitutes the ceramic substrate 51 and a ceramic sheet that constitutes the ceramic substrate 52 on which an electrode material B has been printed. The electrode material B is used to form the conductive layer 53 for the heater 5. Electrode materials for various terminals are printed on the outermost layer of the sheet laminated body thus obtained. Then, on the outermost layer, ceramic materials for forming the trap layer 191 are applied and dried. Subsequently, the sheet laminated body is baked at a temperature of 1450° C. to thereby sinter the ceramic materials and electrode materials. Thus, the gas sensor element 1 is obtained. Note that the sintering temperature can be adjusted within a range of 1400 to 1500° C., for example.

Figure 6:
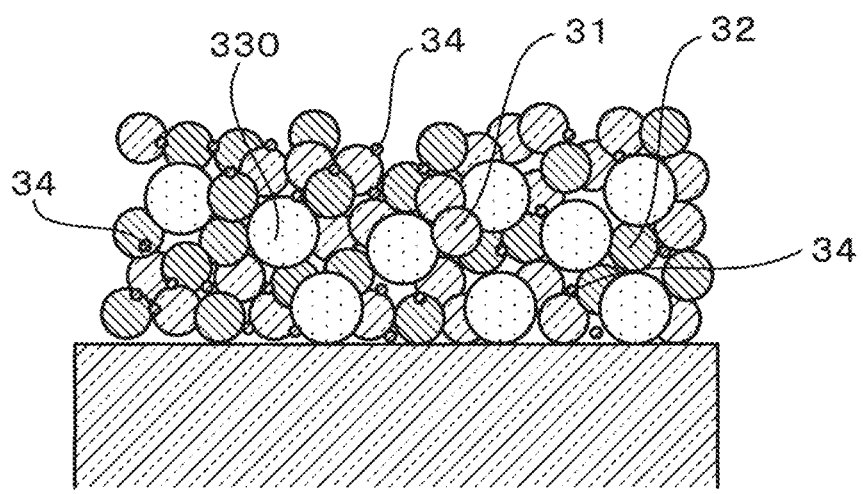
FIG. 6 is a cross-sectional view of electrode materials for a sensor electrode printed on a ceramic sheet for the solid electrolyte body, according to the first embodiment.
Figure 7:
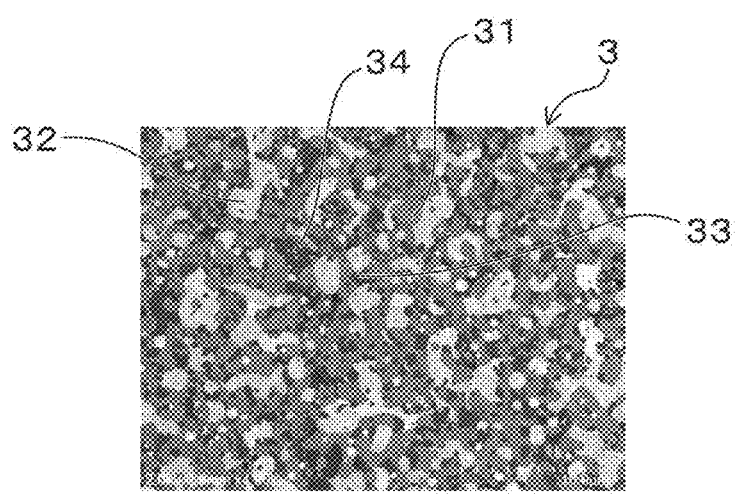
FIG. 7 illustrates a photograph of the sensor electrode obtained as a backscattered electron image using a scanning electron microscope, according to the first embodiment.

As shown in FIG. 6, the sensor electrode 3 is formed of an electrode material containing at least the solid electrolyte 31, precious metal 32, and combustible material 330. Since the combustible material 330 disappears during baking, the sensor electrode 3 is formed with a large number of pores. As the combustible material 330, a material disappearing at sintering temperatures can be used; for example, various organic materials or the like can be used in addition to carbon.

The electrode material for the sensor electrode 3 may contain a sintering inhibitor 34 for inhibiting sintering of the solid electrolyte 31. In this case, contraction of the sensor electrode 3 is inhibited even when the baking is performed at a high temperature of 1400° C. or higher. Hence, the sensor electrode 3 is prevented from becoming dense due to contraction after sintering. That is, the sintering inhibitor 34 enables baking at a high temperature, and various ceramic materials and metal materials to be sintered by one baking. Furthermore, disappearance of pores of the sensor electrode 3 and significant reduction in the pore size are prevented. As the sintering inhibitor 34, a material more resistant to sintering than the solid electrolyte 31 may be used; for example, an oxide such as alumina, or a nitride such as aluminum nitride or silicon nitride may be used. The sintering inhibitor 34 preferably includes alumina considering that it is a low-cost material and highly effective in inhibiting sintering of the solid electrolyte 31. Furthermore, the electrode material is, for example, in paste form, and may contain various solvents, binders, or the like.

An operation and effect of the present embodiment will be described. As shown in FIG. 1 and FIG. 5, the gas sensor element 1 has the sensor electrode 3 including a porous body with a large number of pores 33. The peak pore size of the sensor electrode 3 is adjusted within a specific low range of 0.03 to 0.3 μm. This adjustment increases the three-phase interface between the measurement gas $G_1$, precious metal 32 in the sensor electrode 3, and solid electrolyte body 2 or solid electrolyte 31. The measurement gas $G_1$ is introduced from the exterior into the measurement gas surface 21 side of the solid electrolyte body 2. The sensor electrode 3 can thus convert molecules, such as nitrogen oxides, contained in the measurement gas $G_1$ into ions, such as oxygen ions, with greater efficiency. This results in lower electrode interface resistance, which reduces the detection error of the gas sensor element 1. Consequently, the gas sensor element 1 provides sensor outputs with smaller variations and sufficient stability.

As shown in FIG. 5, the sensor electrode 3 preferably contains the sintering inhibitor 34 for inhibiting sintering of the solid electrolyte 31. In this case, contraction of the sensor electrode 3 is prevented during high-temperature baking. This allows various ceramic materials and electrode materials constituting the gas sensor element 1 to be sintered at high temperatures, requiring only one sintering process. Furthermore, pores are prevented from becoming smaller and eliminated during sintering. This allows the peak pore size of the sensor electrode 3 to be easily adjusted within the above range. Note that in the present embodiment, the gas sensor element 1 has the pump electrode 42, monitor electrode 43, trap layer 191, and the like, but the pump electrode 42, the monitor electrode 43, and the trap layer 191 may not be formed.

FIG. 7 shows an example backscattered electron image of the sensor electrode 3 acquired with a scanning electron microscope (SEM), in the gas sensor element 1 of the present embodiment. FIG. 7 shows a surface of the sensor electrode 3, and is an SEM image produced at an accelerating voltage of 2.0 kV and 4000× magnification. As the scanning electron microscope, an S-3400N manufactured by Hitachi High-Technologies Corporation was used. As shown in FIG. 7, the components constituting the sensor electrode 3 are distinguished by the contrast of the backscattered electron image. Specifically, the precious metal 32 is shown in a very light gray and is shown in a lightest gray among a group including the precious metal 32, solid electrolyte 31, sintering inhibitor 34, and pore 33. The solid electrolyte 31 is shown in a gray; the sintering inhibitor 34, a very dark gray; and the pore 33, a black. That is, in the backscattered electron image of the sensor electrode 3, the precious metal 32 is shown in the color closest to white, and the colors of the solid electrolyte 31, sintering inhibitor 34, and pore 33 are closer to black in this order. Thus, the components 31, 32, 33, and 34 constituting the sensor electrode 3 are distinguished by the contrast of the SEM backscattered electron image.

Second Embodiment

Figure 8:
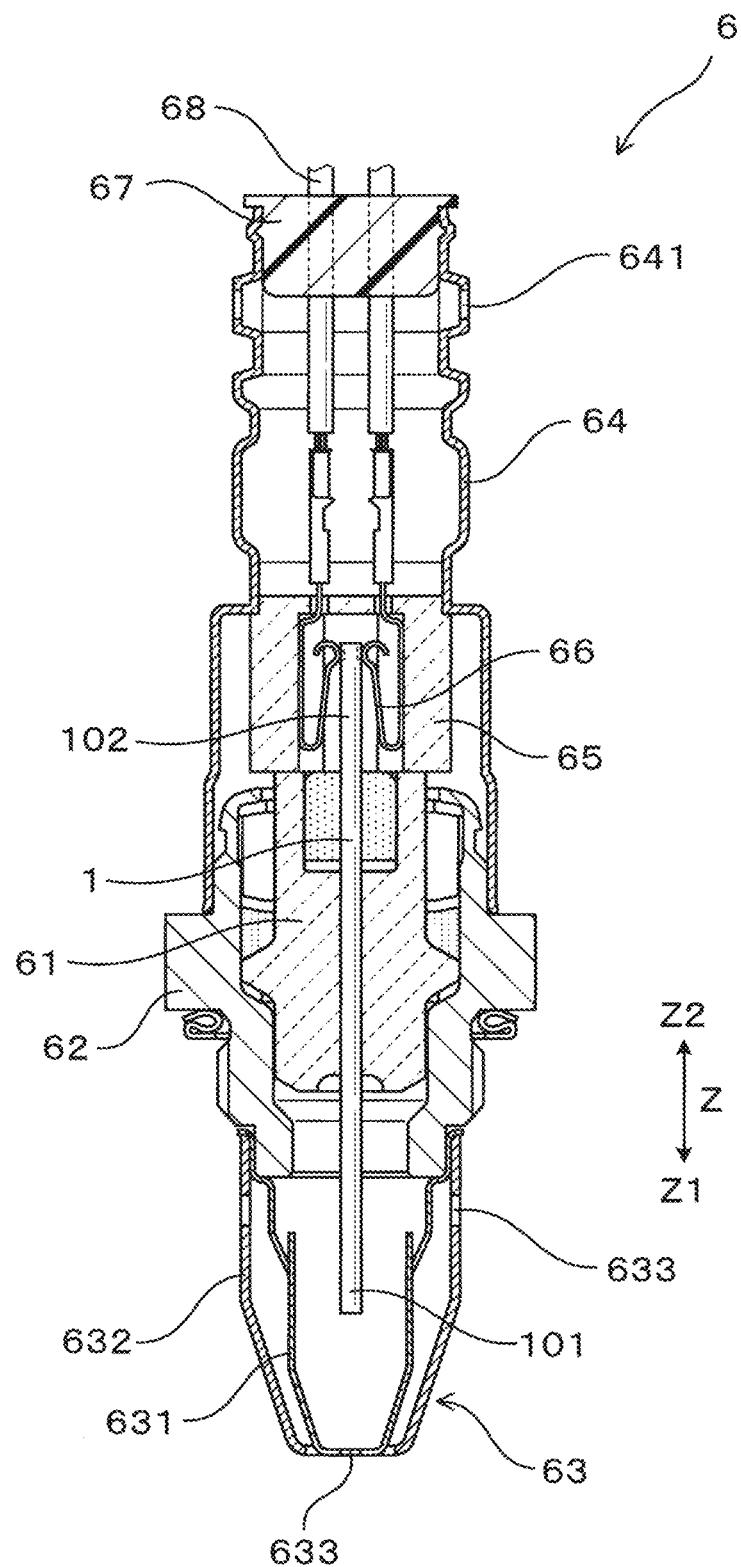
FIG. 8 is a cross-sectional view of a gas sensor according to a second embodiment.

An embodiment of a gas sensor including the gas sensor element will be described with reference to FIG. 8. In this description, the term "axial end side" refers to one side of the gas sensor in an axial direction and a side on which the gas sensor is exposed to the measurement gas. The term "axial proximal side" refers to the opposite side to the axial distal side in the axial direction of the gas sensor. As shown in FIG. 8, a gas sensor 6 of the present embodiment includes the same long plate-like gas sensor element 1 as in the first embodiment, and the longitudinal direction of the gas sensor element 1 corresponds to an axial direction Z of the gas sensor. In the gas sensor element 1, the pump electrode 42, sensor electrode 3, monitor electrode 43, and reference electrode 41 are provided on the axial distal side of the gas sensor 6. The axial distal side and the axial proximal side are referred to as a distal side and a proximal side, respectively. The distal side and the proximal side are also a Z1 side and a Z2 side shown in FIG. 8, respectively. Therefore, the distal side and the proximal side can also be indicated as a distal side Z1 and a proximal side Z2, respectively. A distal end portion 101 of the gas sensor element 1 protrudes from a housing 62 to the distal side Z1 and is exposed to the measurement gas. Furthermore, each lead portion connected to the electrodes 41, 42, 43, and 3 and to the conductive layer 53 of the heater 5 is provided in a proximal end portion 102 of the gas sensor element 1.

The gas sensor element 1 includes a distal-side ceramic insulator 61, the housing 62, a distal-side cover 63, and a proximal-side cover 64. The distal-side ceramic insulator 61 holds the gas sensor element 1. The housing 62 holds the distal-side ceramic insulator 61. The distal-side cover 63 is provided on the distal side of the housing 62. The proximal-side cover 64 is provided on the proximal side of the housing 62. The distal-side cover 63 includes an inner cover 631 and an outer cover 632 provided outside the inner cover 631. The distal end portion 101 of the gas sensor element 1 is covered with the inner cover 631 and the outer cover 632. The inner cover 631 and the outer cover 632 are formed with gas circulation holes 633 for introducing or discharging the measurement gas.

On the proximal side Z2 of the distal-side insulator 61, a proximal-side insulator 65 is provided that has a spring terminal 66 therein. The spring terminal 66 connected to a lead wire 68 is in contact with the respective lead portions in the proximal end portion 102 of the gas sensor element 1. The proximal-side cover 64 is formed with gas circulation holes 641 through which the reference gas is introduced into or discharged from the reference gas chamber 15 of the gas sensor element 1. Furthermore, the proximal-side cover 64 holds a rubber bush 67 for holding the lead wire 68.

The gas sensor 6 of the present embodiment includes the gas sensor element 1 having the same configuration as that of the first embodiment. Consequently, the gas sensor element 1 provides sensor outputs with smaller variations and sufficient stability. Note that of the reference signs used in the second embodiment, the same reference signs when used in embodiments indicate the same components and the like in those different embodiments, unless otherwise indicated.

EXAMPLE 1

Example 1 examines the relationship between the peak pore size of the sensor electrode 3 of the gas sensor element 1 and a detection error of NOx concentration and the relationship between the peak pore size and a specific resistance. First, a plurality of gas sensor elements 1 were created, each including a sensor electrode 3 with a different peak pore size, and the peak pore size of the sensor electrodes 3 was measured. The peak pore size of the sensor electrode 3 can be controlled by adjusting the size (grain size) of combustible material, the amount of combustible material added, the amount of sintering inhibitor added, or the like. Furthermore, sensor electrodes with no pores can be formed without using the combustible material. The other configurations of the gas sensor element of this example are the same as those of the first embodiment.

Figure 9:
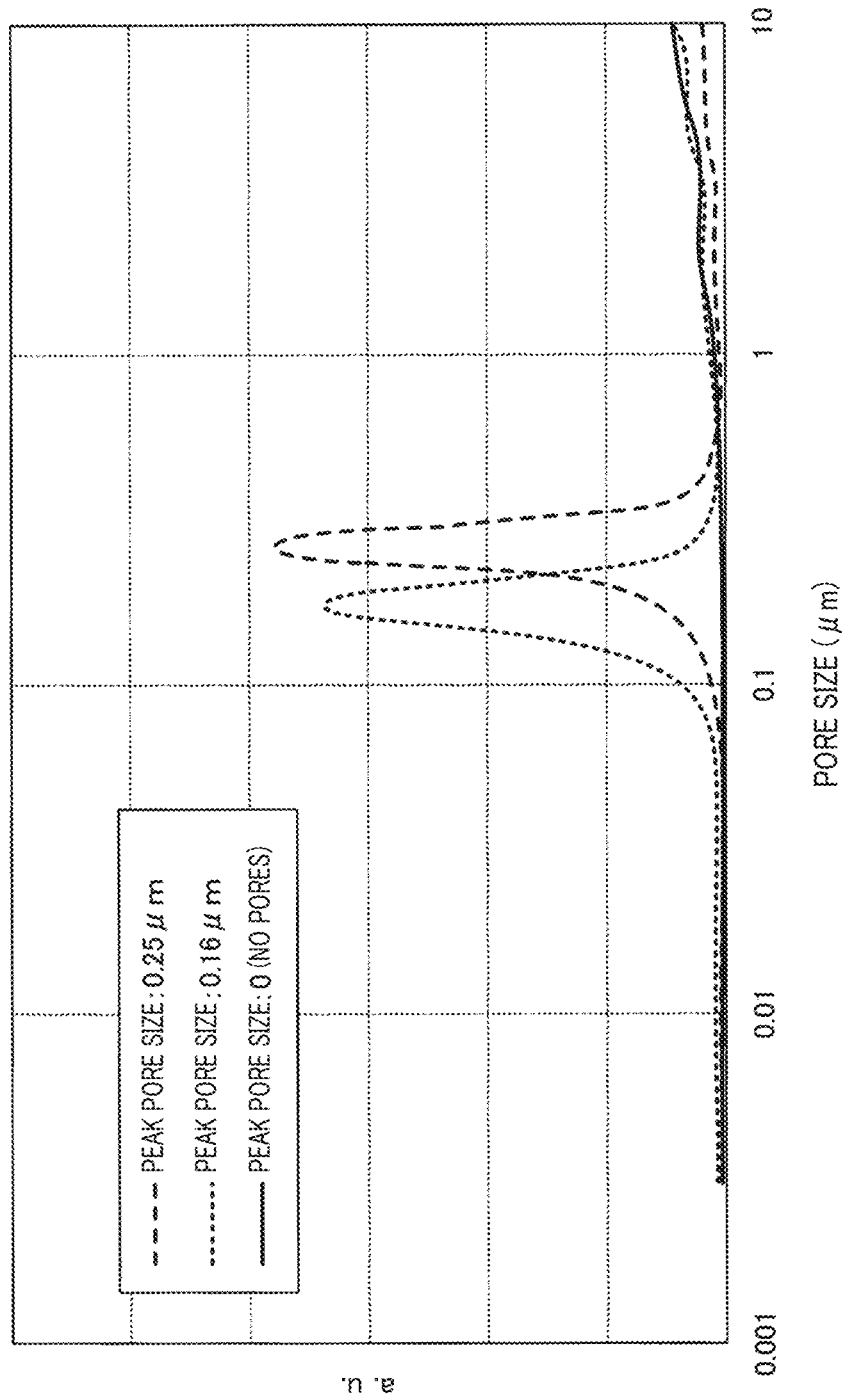
FIG. 9 is a graph showing a pore size distribution of the sensor electrode, according to Example 1.

The peak pore size was measured using a composite device. The composite device can simultaneously perform micromachining with a focused ion beam (FIB) and high-resolution observation with an SEM. This is called FIB-SEM technique. Specifically, the peak pore size of the sensor electrodes 3 was measured with the FIB-SEM technique, using an "NB5000" manufactured by Hitachi High-Technologies Corporation. The measurement was performed under the conditions that the accelerating voltage was 40 kV, and the continuous processing pitch was 212 nm, and "Amira" of Visualization Sciences Group (VSG) Corporation was used as 3D modeling software. FIG. 9 shows one example of the result. In FIG. 9, the horizontal axis represents the peak pore size (unit: μm) and the vertical axis represents an optional unit (a. u.). FIG. 9 shows a measurement result of a sensor electrode with the peak pore size of 0.25 μm, a measurement result of a sensor electrode with the peak pore size of 0.16 μm, and a measurement result of a sensor electrode with no pore. Note that the peak pore size of the sensor electrode 3 in this description was measured by the above FIB-SEM technique. The measurement result demonstrates no differences between the measurement result by the FIB-SEM technique and the measurement result by the known mercury penetration method.

Figure 10:
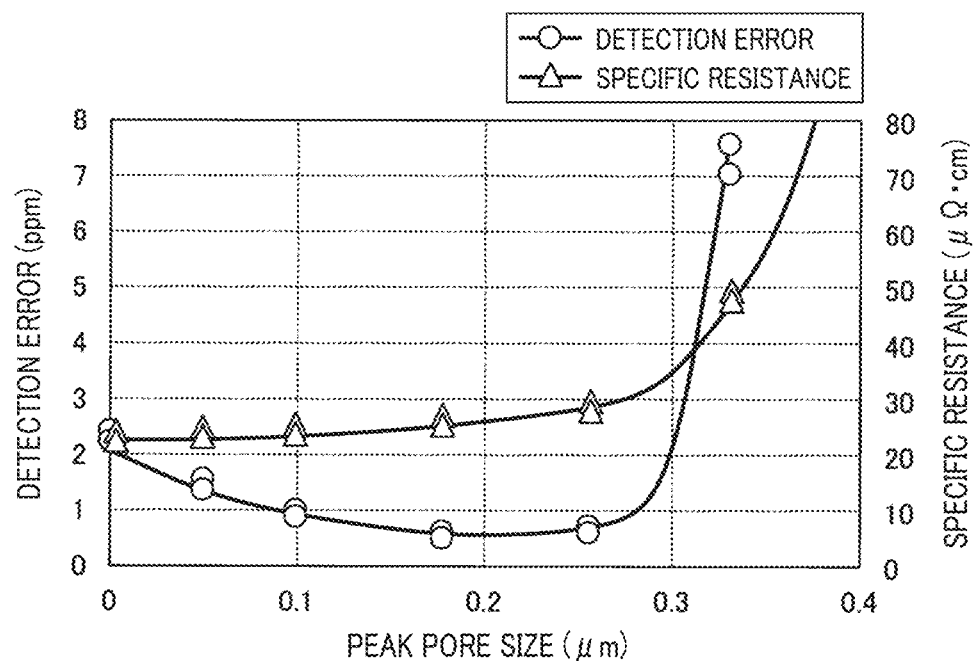
FIG. 10 is a graph showing the relationship between the peak pore size of the sensor electrode and a detection error of NOx concentration and the relationship between the peak pore size and a specific resistance, according to Example 1.

The NOx concentration was detected with the gas sensors 6 fabricated using the gas sensor elements 1 including the sensor electrodes 3 each with a different peak pore size. Then, the detection error of NOx concentration was measured. As the measurement gas for the detection, a gas mixture of NOx and nitrogen was used. In the gas mixture, the NOx concentration is 100 ppm, the $O_2$ concentration is 0, and the rest is $N_2$. FIG. 10 shows the relationship between the peak pore size and the detection error. FIG. 10 also shows the relationship between the peak pore size and the specific resistance of the sensor electrode.

As can be seen from FIG. 10, the detection error and the specific resistance greatly increased in the sensor electrode 3 with a peak pore size exceeding 0.3 μm. The detection error also increased in the peak pore size of less than 0.03 μm. This result indicates that the peak pore size of the sensor electrode is preferably 0.03 to 0.3 μm to reduce variations in the sensor outputs while providing sufficient electrical conductivity. Furthermore, to stabilize good electrical conductivity and the sensor outputs at higher levels, the peak pore size of the sensor electrode is more preferably 0.1 to 0.28 μm.

EXAMPLE 2

Figure 11:
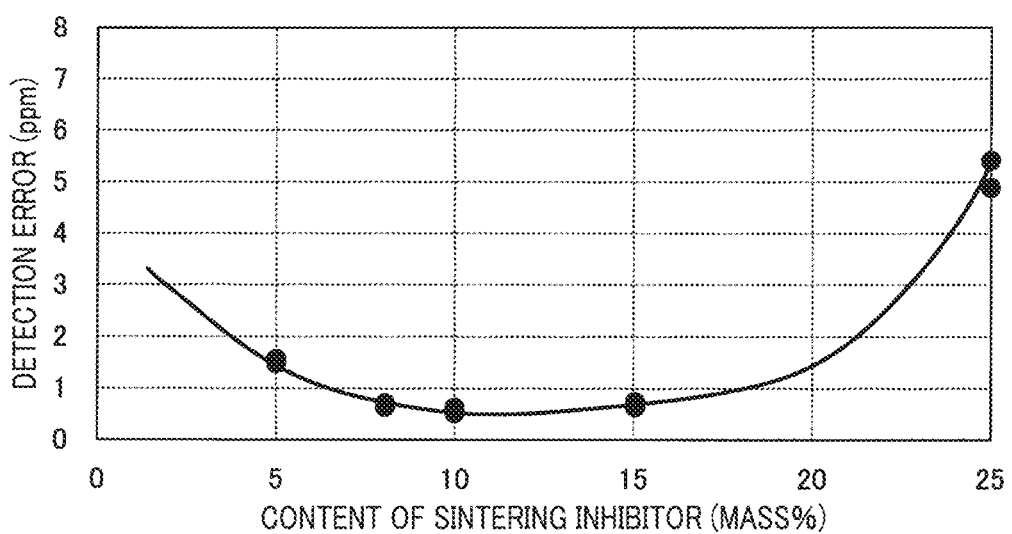
FIG. 11 is a graph showing the relationship between a content of a sintering inhibitor in the sensor electrode and a detection error, according to Example 2.

Example 2 examines the relationship between the content of a sintering inhibitor 34 in the sensor electrode 3 of the gas sensor element 1 and the detection error of NOx concentration. First, a plurality of gas sensor elements 1 were created, each including a sensor electrode 3 with a different content of sintering inhibitor 34. Specific configurations of the gas sensor element 1 are similar to those of the first embodiment. Then, the detection error of NOx concentration was measured for the gas sensor 6 created using each gas sensor element 1. FIG. 11 shows the relationship between the content of sintering inhibitor and the detection error.

As can be seen from FIG. 11, the detection error of NOx concentration in the sensor electrode 3 can be reduced by adjusting the content of sintering inhibitor 34 in the sensor electrode 3 within a range of 5 to 20 mass %. To further reduce the detection error, the content of sintering inhibitor 34 in the sensor electrode 3 is more preferably within a range of 8 to 15 mass %. The content of sintering inhibitor 34 can be measured by composition analysis of an SEM backscattered electron image of the sensor electrode 3 as shown in FIG. 7. As shown in the first embodiment, the sintering inhibitor 34 can be distinguished by the contrast of the backscattered electron image. The composition can be analyzed by Energy-dispersive X-ray spectroscopy (EDX). In EDX, an analytical range is specified using EMAX ENERGY manufactured by HORIBA Ltd., and quantitative analysis of the composition was performed from x-ray energy peaks generated by electron beam irradiation.

EXAMPLE 3

Figure 12:
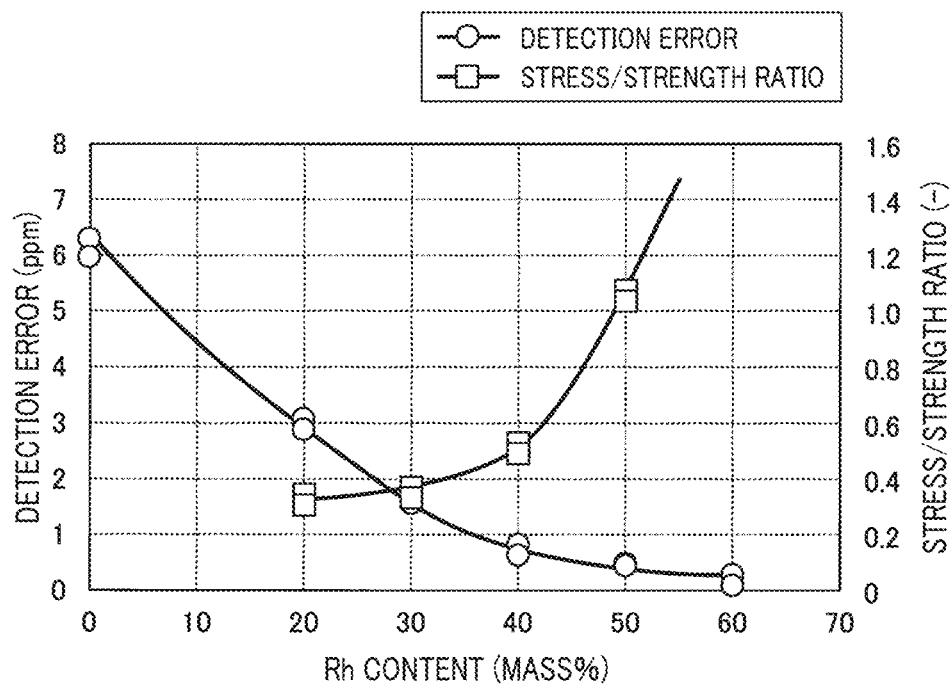
FIG. 12 is a graph showing the relationship between an Rh content of a precious metal in the sensor electrode and a detection error of NOx concentration and the relationship between the Rh content and a stress/strength ratio, according to Example 3.

Example 3 examines the relationship between the Rh content in the precious metal 32 contained in the sensor electrode 3 and the detection error of NOx concentration and the relationship between the Rh content and a stress/strength ratio. The precious metal 32 contained in the sensor electrode 3 is a Pt—Rh alloy as in the first embodiment. First, a plurality of gas sensor elements 1 each with a sensor electrode 3 were fabricated. These sensor electrodes 3 have different Rh contents in the Pt—Rh alloy. Specific configurations of the gas sensor element 1 of this example are similar to those of the first embodiment. Then, the detection error of NOx concentration was measured for the gas sensor 6 created using each gas sensor element 1. FIG. 12 shows the relationship between the content of Rh and the detection error. Furthermore, a thermal stress (i.e., stress) against cold and heat assumed by CAE analysis was calculated and an electrode peel strength (i.e., strength) was calculated. Then, the stress/strength ratio was obtained from a ratio of the calculated values. FIG. 12 shows the result.

As can be seen from FIG. 12, the more the content of Rh, the higher the stress/strength ratio, and the more easily the peeling of the sensor electrode 3 occurs. To prevent the peeling of the sensor electrode 3, the content of Rh in the precious metal 32 is preferably less than 50 mass %. The content of Rh is more preferably not more than 45 mass %, and still more preferably not more than 40 mass %. Furthermore, as can be seen from FIG. 12, as the content of Rh increases, the detection error of NOx concentration in the sensor electrode decreases. To further reduce the detection error, the content of Rh is preferably not less than 20 mass %, more preferably not less than 25 mass %, and still more preferably not less than 30 mass %.

The content of Rh in the precious metal can be measured by composition analysis of an electrode surface by X-ray photoelectron spectroscopy (XPS).

EXAMPLE 4

Figure 13:
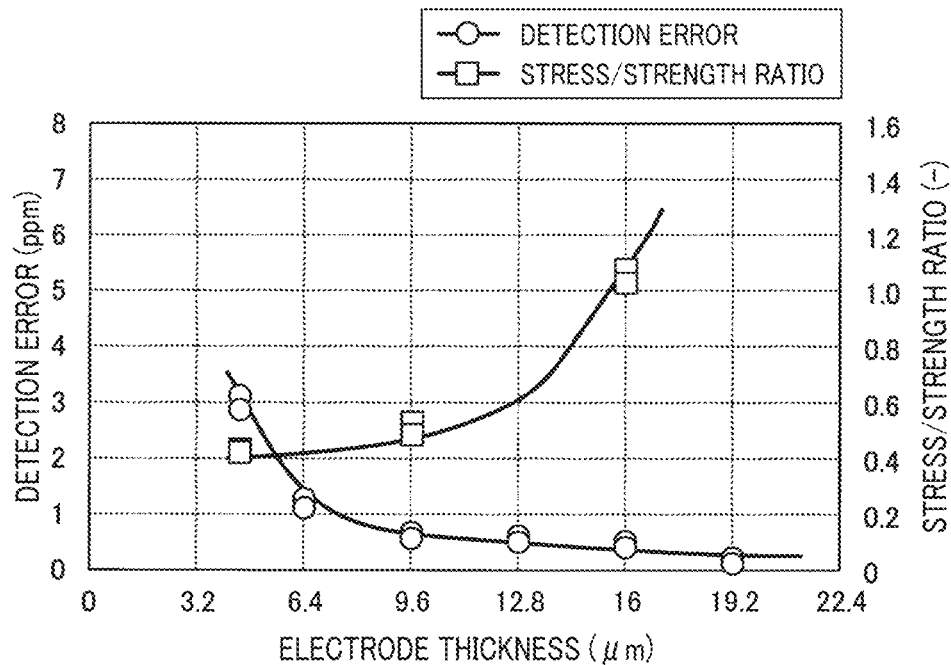
FIG. 13 is a graph showing the relationship between the thickness of the sensor electrode and a detection error of NOx concentration and the relationship between the thickness and a stress/strength ratio, according to Example 4.

Example 4 examines the relationship between the thickness T of the sensor electrode 3 of the gas sensor element 1 and the detection error of NOx concentration and the relationship between the thickness T and a stress/strength ratio. First, a plurality of gas sensor elements 1 were produced each having a sensor electrode 3 with a different thickness T (see FIG. 1). Specific configurations of the gas sensor element 1 are similar to those of the first embodiment. Then, the detection error of NOx concentration was measured for the gas sensor 6 created using each gas sensor element 1. FIG. 13 shows the relationship between the thickness T of the sensor electrode 3 and the detection error. Furthermore, the stress/strength ratio was obtained similarly to Example 3. FIG. 13 shows the relationship between the thickness of the sensor electrode and the stress/strength ratio.

As can be from FIG. 13, the thicker the sensor electrode 3, the higher the stress/strength ratio, and the more easily the peeling of the sensor electrode 3 occurs. In terms of preventing peeling, the thickness of the sensor electrode 3 is preferably 16 μm or less. The detection error decreases with increasing thickness of the sensor electrode 3. Thus, in terms of further reducing the detection error, the thickness of the sensor electrode is preferably 5 μm or more, and more preferably 10 μm or more.

The technique of the present disclosure is not limited to the above embodiments, and can be applied to various embodiments without departing from the spirit. For example, the configuration of the above sensor electrode provides similar effects, even if it is applied to a gas sensor element for an air-fuel ratio sensor (i.e., A/F sensor), or an oxygen sensor, in addition to a gas sensor element for a NOx sensor. Furthermore, as in the first embodiment, the configuration of the above sensor electrode can be employed in not only a long plate-like gas sensor element but also a bottomed cylindrical gas sensor element.

REFERENCE SIGNS LIST

1 . . . Gas sensor element
2 . . . Solid electrolyte body
3 . . . Sensor electrode
31 . . . Solid electrolyte
32 . . . Precious metal
33 . . . Pore
41 . . . Reference electrode
6 . . . Gas sensor

The invention claimed is:

1. A gas sensor element, comprising at least:
a solid electrolyte body having oxygen ion conductivity and including a measurement gas surface to be exposed to a measurement gas introduced from the exterior and a reference gas surface to be exposed to a reference gas introduced from the exterior;
a sensor electrode provided on the measurement gas surface of the solid electrolyte body; and
a reference electrode provided on the reference gas surface of the solid electrolyte body, wherein
the sensor electrode includes a porous body containing a solid electrolyte having oxygen ion conductivity, a precious metal and a sintering inhibitor for suppressing sintering of the solid electrolyte, a peak pore size of the sensor electrode being 0.03 μm to 0.28 μm, and the content of the sintering inhibitor being 8 to 15 mass %.

2. The gas sensor element according to claim 1, wherein the precious metal contains Pt and Rh.

3. The gas sensor element according to claim 1, wherein a content of Rh in the precious metal is less than 50 mass %.

4. The gas sensor element according to claim 1, wherein a thickness of the sensor electrode is 5 μm or more and 16 μm or less.

5. A gas sensor comprising the gas sensor element according to claim 1.

* * * * *